(12) United States Patent
Borzatta et al.

(10) Patent No.: US 6,252,092 B1
(45) Date of Patent: Jun. 26, 2001

(54) PROCESS FOR SYNTHESIS OF 5-ALKYLBENZODIOXOLES

(75) Inventors: Valerio Borzatta, Bologna; Dario Brancaleoni, Sasso Marconi; Christian Battistini, Classe, all of (IT)

(73) Assignee: Endura S.P.A., Bologna (IT)

( * ) Notice: Subject to any disclaimer, the term of this patent is extended or adjusted under 35 U.S.C. 154(b) by 0 days.

(21) Appl. No.: 09/548,763

(22) Filed: Apr. 13, 2000

(30) Foreign Application Priority Data

Apr. 30, 1999 (IT) .......................................... MI99 A000922

(51) Int. Cl.[7] .................................................. C07D 317/50
(52) U.S. Cl. .................................................. 549/434
(58) Field of Search ............................................ 549/434

(56) References Cited

PUBLICATIONS

"Para–Selective Fries Rearrangement of Phenyl Acetate in the Presence of Zeolite Molecular Sieves", *Tetrahedron Letters*, vol. 30, No. 17, pp. 2281–2284, (1989).

"Substitucion Der Carbonyl–Gruppo Durch Die Hydroxy–Gruppe", *Hauben Weil*, E–3 (1983).

C. DevaKumar, "Insect Growth Disrupting Effects of Some 1,3–Benzodioxoles", *Shashpa* 1 (1): 47–52 (1994).

*Primary Examiner*—Joseph K. McKane
*Assistant Examiner*—Taofiq A. Solola
(74) *Attorney, Agent, or Firm*—Abelman, Frayne & Schwab

(57) ABSTRACT

The following description refers to a new process for the synthesis of 5-alkylated benzo[1,3]dioxole, comprising the following steps in sequence: catalytic hydrogenation of 4-acylphenol; acylation; displacement catalysed by Lewis acids; treatment with an inorganic basic compound and hydrogen peroxide; reaction with alkyl dihalides or dialkoxyalkanes.

The process described herein, which yields 5-alkylbenzo[1,3]dioxoles, is economic and can be easily scaled up to industrial size.

10 Claims, 1 Drawing Sheet

PROCESS FOR SYNTHESIS OF 5-ALKYLBENZODIOXOLES

FIELD OF THE INVENTION

The present invention belongs to the field of the synthesis of benzodioxole derivatives, which are particularly useful in perfumery and in the manufacture of insecticides.

PRIOR ART

Various natural substances, such as flavones and alkaloids, which contain the methylenedioxy-1,2-benzene group (also known as benzo[1,3]dioxole) are biologically active. For example, benzo[1,3]dioxole derivatives are used to treat liver disorders (*Chem. Abstracts*, 1990, 113: 52534).

Said derivatives have found extensive application in perfumery and in the manufacture of flavours and insecticides. Compounds containing the benzo[1,3]dioxole group, which show insecticide action, have been described in several publications (cf. e.g. *Bull. Soc. Chim. France*, 1964, 1892–1895).

Particularly interesting are the 5-substituted benzo[1,3]dioxole derivatives, such as for example 5-(2-propenyl)-benzo[1,3]dioxole (safrole), a constituent of many essential oils and one of the chief constituents of sassafras oil (75% approx.) (Oswald et al., *Biochim. Biophys. Acta*, 1971, 230, 237). A further important 5-substituted derivative is 5-(1-propenyl)-benzo[1,3]dioxole (isosafrole), an essence used in perfumery and as a deodoriser for soap. Isosafrole is also used in the synthesis of piperonal (heliotropin, benzo[1,3]dioxole-5-carboxyaldehyde), another essence utilised in the perfume and flavour industry. Also 5-hydroxymethyl-benzo[1,3]dioxole (piperonyl alcohol) and derivatives thereof are of most interest for the aforesaid industrial areas.

Particularly interesting are the benzo[1,3]dioxoles substituted in position 5 with an alkyl group, since they may be used as key reagents in the synthesis of the aforementioned products of industrial importance as well as of other products, such as piperonyl butoxide, an active ingredient exhibiting insecticide action. Furthermore, 5-alkylbenzo[1,3]dioxoles, on their own, show biological activity as inhibitors of liver enzymes (*Shashpa*, 1994 (1)1, 47–52).

Therefore, the need for effective processes for the synthesis of 5-allylbenzo[1,3]dioxoles is deeply felt.

Typically, the formation of the benzo[1,3]dioxole ring is obtained by causing catechol (1,2-dihydroxybenzene) to react with methylene halides (e.g. $CH_2Cl_2$) in a dipolar aprotic solvent and in a basic environment (*Tetrahedron Lett.* 1991, 32 (22), p. 2464). Unfortunately, this reaction to yield 5-alkylated benzo[1,3]dioxole can be hardly exploited in indusrtial-scale plants: in fact, the high cost of 4-alkylcatechols, which are required for the synthesis of said derivatives, makes said synthesis economically unprofitable. This problem cannot be solved by a direct synthesis 4-alkylcatechols, as it produces a mixture of undesired isomers (J. March, *Advanced Organic Chemistry*, McGraw-Hill Inc., 1968, 406–409) or requires the use of reagents in particularly severe conditions, e.g. hydrofluoric acid in the liquid state (CS-160524), which factors increase the process cost.

In view of the foregoing limitations, there is an urgent need for identifying an effective route for the synthesis of 5-alkylated benzo[1,3]dioxoles. In particular, the synthesis to be developed must be little expensive and easily reproducible on a industrial scale.

SUMMARY

It has surprisingly been found a process for the synthesis of 5-alkylated benzo[1,3]dioxoles, which makes up for the aforesaid cons. Said process comprises the following steps in sequence: catalytic hydrogenation of 4-acylphenol; acylation; displacement catalysed by Lewis acids; treatment with an inorganic basic compound and hydrogen peroxide; reaction with alkyl dihalides or dialkoxyalkanes.

The process described herein, which yields 5-alkylbenzo[1,3]dioxoles, is economic and can be easily scaled up to industrial size.

DETAILED DESCRIPTION OF THE INVENTION

Figure 1:
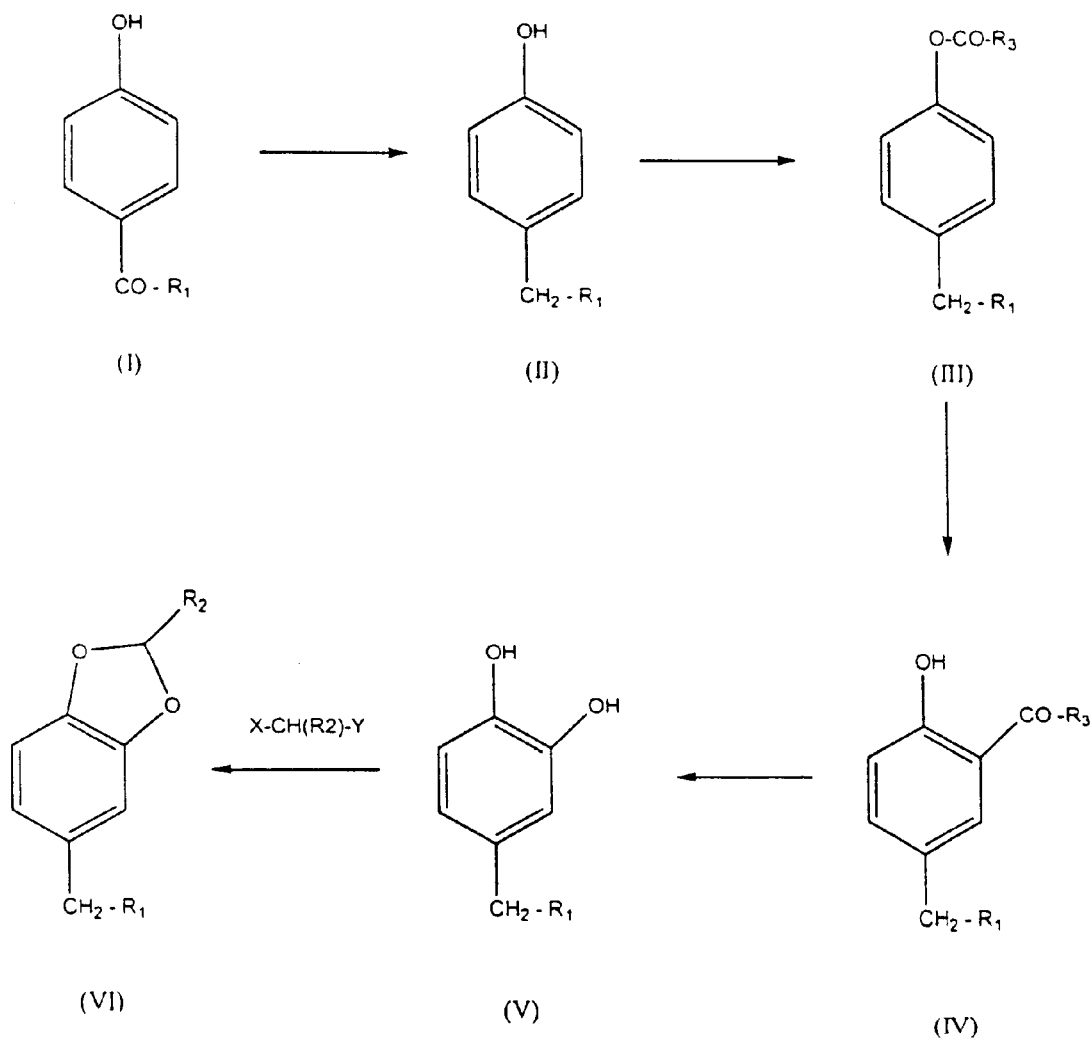
FIG. 1: scheme of the synthesis of 5-alkylbenzo[1,3]dioxoles

It is an object of the present invention to provide a process for the synthesis of 5-alkylbenzo[1,3]dioxoles. The process, illustrated in FIG. 1, is characterised by the following steps:

(a) catalytic hydrogenation of 4-acylphenol of formula (I), where $R_1$ is a $C_1$–$C_{17}$ alkyl, to give 4-alkylphenol of formula (II);

(b) acylation of compound (II) with an acyl group containing up to 3 carbon atoms, to give a compound of formula (III), where $R_3$ is methyl or ethyl;

(c) treatment of compound (III) with a Lewis acid to give 4-alkyl-2-acylphenol (IV);

(d) treatment of compound (IV) at 0° C. to 25° C. with hydrogen peroxide and a hydroalcoholic solution containing an inorganic basic compound, in a basic compound/compound (IV) molar ratio equal to 0.8:1 to 2:1, preferably 1:1 to 1.5:1, to give 4-alkylcatechol (V);

(e) cyclisation of compound (V) with a compound of formula X-CH($R_2$)—Y, where X and Y, identical or different, may be each selected: (i) from the group consisting of chlorine, bromine, iodine, or (ii) from the group consisting of $CH_3O$—, $C_2H_5O$—, and where $R_2$ is H, or a $C_1$–$C_3$ alkyl, to give 5-alkylbenzo[1,3]dioxole (VI).

Step (a) of the process being the object of the invention consists in the catalytic hydrogenation of 4-acylphenol of formula (I) to give 4-alkylphenol of formula (II).

Radical $R_1$ is an alkyl containing 1 to 17 carbon atoms, preferably 1 to 5.

4-Acylphenols (I) are commercially available. Hydrogenation is conducted at a pressure of 0.5 to 60 bars and at a temperature of 10° C. to 100° C., in the presence of the catalysts commonly used in catalytic hydrogenations, either as are or supported on an inert matrix. Typical examples of said catalysts are $PtO_2$, PtO, Ni Raney, Pd on carbon, Pd on barium sulphate, Pt on carbon, Pt on alumina, Pd on alumina.

The reaction is carried out with or without an appropriate solvent. Alcoholic solvents, such as methanol, ethanol, isopropanol, and butanol, are preferably used.

Step (a) gives excellent yields even under environmental conditions (1 bar and 20° C.); therefore, it can be applied to large industrial-scale plants, thereby effecting a considerable saving in energy.

Step (b) of the process being the object of the invention consists in the acylation of the hydroxyl of alkylphenol of formula (II). The acylation, which is carried out by techniques known in the art, is performed by causing compound (II) to react with an aliphatic acid selected from the group consisting of acetic acid and propionic acid and respective chlorides and anhydrides.

Should the reaction be effected with an acid, it will be carried out with or without a suitable inert solvent and with an acid catalyst. Preferably, the reaction solvents are benzene, toluene, xylene, mesitylene, dichloroethane, tetrachloroethane; most preferably toluene. Preferably, the acid catalysts are sulphuric, methanesulphonic, p-toluenesulphonic, trifluoroacetic, trichloroacetic acids and most preferably p-toluenesulphonic acid. The reaction temperature is preferably the temperature at which the water that forms during the reaction is removed by azeotropic distillation. Should the reaction be carried out with an acid chloride, it will be performed in the presence of an appropriate inert, 'solvent and of a suitable hydrochloric acid acceptor, selected among organic bases. Preferably, the reaction solvents are benzene, toluene, xylene, cyclohexane, methylcyclohexane and most preferably toluene. Preferably, the organic bases are triethylamine, tributylamine, pyridine, methylpyridine, lutidine and most preferably triethylamine. The reaction is carried out between 0° C. and 80° C., conveniently between 0° C. and 25° C. The base is used in the range from 1:1 to 1:3 mols per mole of acid chloride and preferably in the range from 1:1 to 1.5:1.

Should the reaction be carried out with an anhydride, it will be effected with or without an inert solvent. Preferably, the reaction solvents are benzene, toluene, mesitylene, cyclohexane, methylcyclohexane, dichloroethane, tetrachloroethane and most preferably toluene. The quantity of anhydride used ranges from 1:1 to 2:1 per mol of compound (II), and the reaction is carried out at the reflux temperature of the solvent or of the anhydride used as reagent when the reaction is carried out in bulk.

Step (b) yields acylated product (III), where $R_3$ is methyl or ethyl and $R_1$ has the above meanings.

Step (c) consists in the treatment of compound (III) with a Lewis acid to give 4-alkyl-2-acylphenol (IV), where $R_1$ ed $R_3$ have the above meanings. Typical Lewis acids are: $AlCl_3$, $AlBr_3$, $BCl_3$, $BBr_3$, $BF_3$, $ZnCl_2$, $FeCl_2$, optionally supported on an inert matrix, such as alumina. Excellent results have been obtained using, as acid catalysts, zeolites in a Si/Al ratio ranging from 8 to 100, preferably from 10 to 60.

Reaction (c) is carried out with or without a suitable inert solvent. Examples of said solvents are cyclohexane, methylcyclohexane, Decalin, nitrobenzene, chlorobenzene, dichloroethane, tetrachloroethane.

The reaction is carried out at the solvent reflux temperature. Should the reaction be conducted in bulk, the reaction temperature will range from 80° C. to 140° C., more conveniently from 90° C. to 120° C.

Reaction (c) yields displacement product (IV) where $R_1$ and $R_3$ have the above meanings.

Step (d) consists in the treatment of compound (IV) at a temperature of 0° C. to 25° C. with a hydroalcoholic solution containing an inorganic basic compound and with hydrogen peroxide, in a basic compound/compound (IV) molar ratio equal to 0.8:1 to 2:1, preferably 1:1 to 1.5:1.

The hydroalcoholic solution is preferably a 1:1 (v/v) water-methanol or water-ethanol mixture.

Examples of inorganic basic compounds are sodium bicarbonate, sodium carbonate, potassium bicarbonate, potassium carbonate, sodium hydroxide and potassium hydroxide. The preferred basic compound is sodium bicarbonate.

Hydrogen peroxide is used as a solution between 2% and 70% by wt., preferably between 5% and 40% by wt. and more preferably between 5% and 25% by wt.

Preferably, compound (IV), the inorganic basic compound and hydrogen peroxide are used in equimolar amounts.

In a preferred embodiment of the reaction, once the hydroalcoholic solution containing the basic compound has been prepared, it is added with compound (IV) first and then with hydrogen peroxide.

Reaction (d) is a variation of the oxidation described in *Houben-Weil* E-3, 1983, p.293, specifically for salicylaldehyde, i.e. reaction (d) is directly conducted on acylated compound (IV) and not on the corresponding aldehydic derivative, hardly obtainable under the present conditions. The reaction affords compound (V) in very high yields.

Also reaction (d) is carried out under environmental conditions and, therefore, can be easily applied to industrial-scale plants.

In step (e) the benzodioxole ring is closed by reaction with a compound of formula $X—CH(R_2)—Y$, where X and Y, identical or different, may be each selected (i) from the group consisting of chlorine, bromine, iodine, or (ii) from the group consisting $CH_3O—$, $C_2H_5O—$, and where $R_2$ is H or a $C_1–C_3$ alkyl. This reaction is effected according to techniques known in the art, as described e.g. in *J. Chem. Soc.* (C), 969, 1202–1204. When X and Y stand for a halogen (e.g. dichloromethane), the reaction is carried out in a dipolar aprotic solvent, such as N,N dimethylformamide (DMF), N,N dimethylacetamide, dimethylsulphoxide in the presence of an inorganic base, such as sodium hydroxide, sodium carbonate, potassium carbonate, and optionally in the presence of a iodine salt, such as NaI, KI, $CaI_2$, at temperature between 70° C. and 150° C. Preferably, compound (V) is dissolved in DMF-dichloromethane mixture; the resulting solution is added to an inorganic base suspension in DMF and dichloromethane, the temperature being kept at 110° C. to 130° C. throughout the addition.

When X and Y stand for $CH_3O—$, and/or $C_2H_5O—$, the reaction is carried out in an inert solvent, such as for example toluene, xylene, mesitylene, in the presence of an appropriate transesterification catalyst, such as for example sodium methoxide, lithium amide, sodium hydride, titanium tetrabutoxide, dimethyltin oxide. The operating temperature is preferably the boiling temperature of the solvent.

The resulting benzodioxoles exhibit a significant biological activity as insecticides. Furthermore, they may be used as key reagents in the synthesis of piperonylic alcohol, safrole, isosafrole and derivatives thereof, useful in perfumery and in the manufacture of insecticides.

These products are easily obtained by oxidation and dehydration of the alkyl residue in position 5, which reactions are well known in the art.

The following examples are conveyed by way of indication, not of limitation, of the present invention.

Experimental Part

EXAMPLE 1A
Synthesis of 4-propyl Phenol

A 500 ml autoclave was fed with 4-hydroxypropiophenone (30 g; 0.2 mols) in methanol (100 ml) and 5% Pd/C (1 g; 50% wet). Once the mixture had been washed with nitrogen, it was hydrogenated at room temperature and atmospheric pressure.

The catalyst was filtered and the product was evaporated in vacuo (40° C./24 mbar). 4-Propyl phenol was obtained in a quantitative yield.

EXAMPLE 1B
Synthesis of 4-propyl Phenol Acetate

4-Propyl phenol (13.6 g; 0.1 mols) was dissolved in dichloroethane (100 ml). The resulting mixture was added with triethylamine (15.2 9; 21 ml, 0.15 mols) at room temperature.

The solution was cooled to 0–3° C. and slowly added with acetyl chloride (9.4 g; 8.6 ml, 0.12 mols) dissolved in dichloroethane (20 ml), the temperature being maintained at 5–10° C.

Once the addition had been completed, the solution was allowed to stir at room temperature for 1 hr and filtered. The organic solution was washed with 2M HCl (50 ml), 2M NaOH (50 ml) and with water (50 ml), dried over anhydrous sodium sulphate, filtered and evaporated to give a colourless oil.

EXAMPLE 1C
Synthesis of 2-acetyl-4-propyl Phenol

4-Propyl phenol acetate (17.8 g; 0.1 mols) was added with aluminium chloride (13.3 g; 0.1 mols).

The reaction was strongly exothermic. The mixture was allowed to stir at 110° C. for 4 hrs, cooled to 0° C. and taken up with dichloroethane (100 ml) and 6N HCl (100 ml). Stirring was continued and the organic phase was separated. The aqueous phase was washed three times with dichloroethane (50 ml) and the organic phases were combined.

The resulting organic phase was washed with a 5% sodium bicarbonate aqueous solution (w/v) (150 ml), dried over anhydrous sodium sulphate, filtered and evaporated in vacuo (40° C./24 mbar) to give a light yellow oil.

EXAMPLE 1D
Synthesis of 4-propyl Catechol

A sodium bicarbonate solution (4.2 g; 50 mmols) in water (25 ml) was added with 2-acetyl-4-propyl phenol (8.6 g; 50 mmols) dissolved in methanol (25 ml).

The resulting mixture, maintained at room temperature, was slowly added with 15% hydrogen peroxide (11.9 g; 52.5 mmols) (%, w/w).

Once the addition had been completed, the mixture was allowed to stir for 4 hrs and evaporated in vacuo (45° C./24 mbar). The aqueous residue was taken up with water (30 ml) and extracted three times with isopropyl ether (50 ml). The organic phase was evaporated in vacuo (30° C./24 mbar) to give a very thick yellow oil.

EXAMPLE 1E
Synthesis of 5-propyl Benzodioxole

4-Propyl catechol (10.7 g; 70 mmols) was dissolved in a 90:10 (v/v) DMF/dichloromethane mixture (17 ml). The resulting solution was added very slowly to a suspension of anhydrous $K_2CO_3$ (14.1 g; 87 mmols) in a 90:10 (v/v) DMF/dichloromethane mixture (85 ml), maintained at 115–120° C.

Once the addition had been completed, the solution was kept at 120–125° C. for additional 3 hrs, cooled and filtered.

The mixture was filtered at 60° C./12 mbar and the residue was taken up with water (30 ml) and extracted with n-hexane (50 ml).

The organic phase was dried over anhydrous sodium sulphate, filtered and dried in vacuo (30° C./24 mbar).

11.2 g of 5-propyl benzo-[1,3]-dioxole was obtained.

What is claimed is:

1. Process for the synthesis of 5-alkylbenzo[1,3]dioxoles comprising the following steps:

(a) catalytic hydrogenation of 4-acylphenol of formula (I), where $R_1$ is a $C_1$–$C_{17}$ alkyl, to give 4-alkylphenol of formula (II)

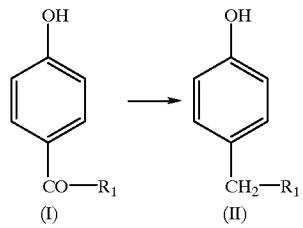

(b) acylation of compound (II) with an acyl group containing up to 3 carbon atoms, to give a compound of formula (III), where $R_3$ is methyl or ethyl

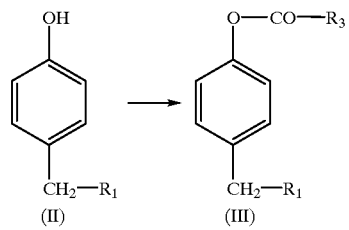

(c) reacting compound (III) with a Lew is acid to give 4-alkyl-2-acylphenol (IV)

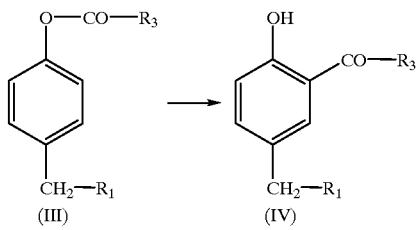

(d) reacting compound (IV) at 0° C. to 25° C. with hydrogen peroxide and a hydroalcoholic solution containing an inorganic basic compound, wherein the basic compound/compound (IV) molar ratio equal to 0.8:1 to 2:1 to give 4-alkylcatechol (V)

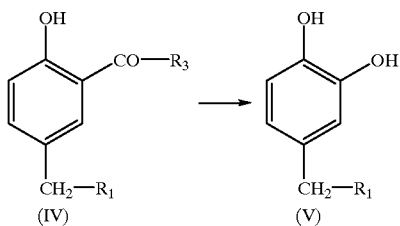

(e) cyclization of compound (V) with a compound of formula X—CH($R_2$)—Y, where X and Y, identical or different, may be each selected: (i) from the group consisting of chlorine, bromine, iodine, or (ii) from the group consisting of $CH_3O$—, $C_2H_5O$—, and where $R_2$ is H, or a $C_1$–$C_3$ alkyl, to give 5-alkylbenzo[1,3]dioxole (VI)

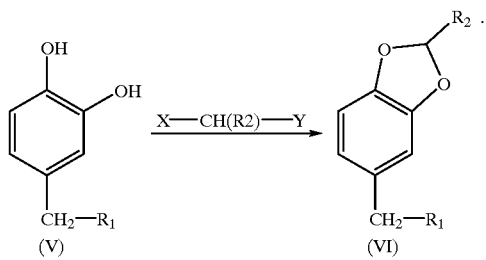

2. The process according to claim 1, wherein $R_1$ is a $C_1$–$C_5$ alkyl.

3. The process according to claim 1, wherein hydrogenation (a) is carried out at 1 bar and 20° C., and is catalysed by a compound selected from the group consisting of $PtO_2$, PtO, Ni Raney, Pd on carbon, Pd on barium sulphate, Pt on carbon, Pt on alumina, Pd on alumina.

4. The process according to claim 1, wherein the Lewis acid used in step (c) is selected from the group consisting of $AlCl_3$, $AlBr_3$, $BCl_3$, $BBr_3$, $BF_3$, $ZnCl_2$, $FeCl_2$, optionally supported on an inert matrix, and zeolites.

5. The process according to claim 1, wherein the inorganic basic compound used in step (d) is selected from the group consisting of sodium bicarbonate, sodium carbonate, potassium bicarbonate, potassium carbonate, sodium hydroxide and potassium hydroxide.

6. The process according to clam 1, wherein compound (IV), the inorganic basic compound and hydrogen peroxide used in step (d), are in equimolar amounts.

7. The process according to claim 1, wherein step (d) comprises the preparation of the hydroalcoholic solution containing the inorganic basic compound, followed by addition of compound (IV) and finally by addition of hydrogen peroxide.

8. The process according to claim 1, wherein in the compound of formula X—CH($R_2$)—Y used in step (e), X and Y are selected from group (i) and the reaction is carried out in a alkaline dipolar solvent, optionally in the presence of a iodine salt.

9. The process according to claim 1, wherein in the compound of formula X—CH($R_2$)—Y used in step (e), X and Y are selected from group (ii) and the reaction is carried out in an inert solvent in the presence of a transesterification catalyst.

10. The process according to claim 9, wherein the transesterification catalyst is selected from the group consisting of sodium methoxide, lithium amide, sodium hydride, titanium tetrabutoxide, dimethyltin oxide.

* * * * *